(12) United States Patent
Tanii et al.

(10) Patent No.: US 7,514,683 B2
(45) Date of Patent: Apr. 7, 2009

(54) SCANNING ELECTRON MICROSCOPE

(75) Inventors: Kazuma Tanii, Hitachinaka (JP); Yuji Kasai, Hitachinaka (JP); Katsuhiro Sasada, Hitachinaka (JP); Eiichi Seya, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 259 days.

(21) Appl. No.: 11/655,275

(22) Filed: Jan. 19, 2007

(65) Prior Publication Data

US 2007/0235646 A1 Oct. 11, 2007

(30) Foreign Application Priority Data

Jan. 20, 2006 (JP) ............................. 2006-012744

(51) Int. Cl.
*H01J 37/28* (2006.01)
(52) U.S. Cl. .................................................... 250/310
(58) Field of Classification Search ................. 250/310, 250/396 R
See application file for complete search history.

(56) References Cited

U.S. PATENT DOCUMENTS 6,444,981 B1 9/2002 Todokoro et al.
6,512,228 B2 * 1/2003 Todokoro et al. ........... 250/310

FOREIGN PATENT DOCUMENTS

| JP | 7-245075 | 9/1995 |
| JP | 11-126573 | 5/1999 |
| JP | 2000-133194 | 5/2000 |
| JP | 2001-52642 | 2/2001 |

* cited by examiner

*Primary Examiner*—Kiet T Nguyen
(74) *Attorney, Agent, or Firm*—McDermott Will & Emery LLP

(57) ABSTRACT

Disclosed is a scanning electron microscope capable of performing speedy focusing by automatically measuring an electrostatic voltage of a surface of a wafer inside a specimen chamber in an accurate, and easy speedy manner, the wafer assuming different electrostatic voltages inside and outside the specimen chamber. The scanning electron microscope that controls optical systems measures an electrostatic voltage of the specimen according to an electrostatic capacitance between the both parts of the divided electrode plate, by dividing an electrode plate into two parts and switching potentials of electrodes obtained by the division with each other, an electrostatic voltage of the specimen based on an electrostatic capacitance between the both parts of the divided electrode plate. The electrode plate is used for applying a retarding voltage and arranged over a specimen.

3 Claims, 4 Drawing Sheets

SCANNING ELECTRON MICROSCOPE

BACKGROUND OF THE INVENTION

1. Field of the Invention

The present invention relates to a scanning electron microscope which scans an electron beam on a surface of a specimen, detects secondary electrons generated from the specimen, and thereby obtains a scanning image of the specimen surface.

2. Description of the Related Art

In recent years, as semiconductor devices have been becoming more highly integrated and finer, scanning electron microscopes have started to be used, in place of optical microscopes, in dimension measurement of and shape evaluation of semiconductor devices in manufacturing processes of the semiconductor devices. In order to automatically and speedily process measurement of mass-manufactured semiconductors, it is necessary to speedily detect each measurement point on a wafer, and, for that purpose, it is necessary to focus an electron beam on a pattern speedily after the electron beam has moved to the each measurement point.

In an electron optical system, a condition for focusing on a wafer is uniquely determined by: an accelerating voltage of electrons irradiated to the wafer; and a height of the wafer. Additionally, the accelerating voltage of the electrons is determined by: an extracting voltage of the electrons; a retarding voltage applied to the wafer so as to decelerate the electrons; and an electrostatic voltage of a surface of the wafer. In order to obtain a desired accelerating voltage, in normal cases, the retarding voltage is controlled in accordance with the electrostatic voltage of the wafer on condition that the extracting voltage has been maintained at a constant level. For example, by measuring a potential of the wafer by use of an electrostatic potential meter grounded outside a specimen chamber, and canceling an influence from the electrostatic voltage of the wafer by feeding back a result of the measurement to the control over the retarding voltage, the accelerating voltage can be maintained at a constant level and thereby can be prevented from affecting the condition for the focusing. On the other hand, in order to measure the wafer height, there has been adopted a method as described in, for example, Japanese Patent Application Laid-open No. Hei11-126573, the method including the steps of: irradiating laser light to the wafer; detecting the wafer height by utilizing reflected light thereof; feeding back, to an objective lens which is one of the electron optical systems, height information obtained thereby; and, at the same time as movement of the electron beam to a measurement point is completed, applying excitation that is necessary for the focusing to the objective lens. By performing the above control over the accelerating voltage and the wafer height at one time, it becomes possible to focus an electron beam at the same time as movement of the electron beam to any measurement point is completed.

However, in recent years, there have been occasionally found wafers each showing a change in electrostatic voltage of a surface thereof when being moved between the outside and the inside of a specimen chamber. For example, there is a wafer that assumes hardly any voltage outside a specimen chamber, but assumes a voltage of several ten to several hundred volts inside the specimen chamber. Such a difference in amount of electrostatic charge between the outside and the inside of the specimen chamber depends on a manufacturing environment intrinsic to the each wafer, and also on a thickness of layer electrically charged. Therefore, such differences are not necessarily constant among those wafers that have undergone the same manufacturing processes. As to each of such wafers, even if a focusing condition is determined on the basis of an electrostatic voltage of the wafer measured by use of an electrostatic potential meter grounded outside a specimen chamber, the focusing condition changes when the electrostatic voltage becomes different inside the specimen chamber. Consequently, because an electron beam cannot be focused in a measurement point, detection of the measurement point ends in failure. Eventually, a supportive operation by an operator comes to be required as the measurement cannot be automatically performed.

As means for solving such a problem, there is, for example, a retarding focus system. As has been mentioned above, a condition for focusing on a wafer is determined by an accelerating voltage of electrons irradiated to the wafer, and a height of the wafer, and this means that, on condition that the wafer height is accurately measured, an accelerating voltage at the time when the wafer is focused is uniquely determined. Accordingly, by changing the focusing condition by changing a retarding voltage thereto with an extracting voltage of electrons being maintained at a constant level, a potential on a surface of the wafer at a measurement point can be back calculated from values of the accelerating voltage, the extracting voltage and the retarding voltage at the time when the wafer is focused. Additionally, there has been a method as described in Japanese Patent Application Laid-open No. 2001-52642 including the steps of: installing plural electrostatic potential meters in a place approximate to a specimen inside a specimen chamber; and feeding back values obtained based on results of measurement thereby to the retarding voltage.

SUMMARY OF THE INVENTION

However, the abovementioned methods involve some problems. First of all, it is not necessarily the case that amounts of electrostatic charges assumed by wafers are constant even among the wafers having undergone the same manufacturing processes. For this reason, in the retarding focus system, an amplitude at the time when the retarding voltage is changed has to be constantly set in a wide range by assuming a case where an amount of electrostatic charge large, whereby focusing comes to take some time. Additionally, such focusing has to be performed with respect to each and every measurement point, thereby coming to hinder speedup of automatic measurement to a large extent. Additionally, a technology having been proposed in Japanese Patent Application Laid-open No. 2001-52642 not only is complicated because of the necessity of installing additional electrostatic potential meters inside the chamber, but also may possibly have a risk that vibration or the like of the electrostatic potential meters inside the specimen chamber negatively affect an electron beam. Additionally, in the case of measuring an electrostatic charge amount in a neighborhood of an edge of the wafer, the measurement is not practical even with plural probes of the electrostatic potential meters being installed around an observation point. This is because, in reality, there are some probes detached from on the wafer. Furthermore, this technology requires work of adjusting the plural potential meters, which are used in combination, so as for them to constantly make the same outputs, and therefore, this technology is complicated. Additionally, these problems have not been solved in scanning electron microscopes described in Japanese Unexamined Patent Application No. Hei7-245075 and Japanese Patent Application Laid-open No. 2000-133194.

The present invention was made in consideration of a situation as described above, and is aiming at providing a scanning electron microscope capable of performing speedy focusing by automatically measuring an electrostatic voltage of a surface of a wafer inside a specimen chamber in an accurate, and easy speedy manner, the wafer assuming different electrostatic voltages inside and outside the specimen chamber.

As a result of ardent researches in consideration of the above problem to be solved, the present inventor has reached a finding that, by dividing an electrode plate into two parts, and switching potentials of electrodes obtained by the division with each other, an electrostatic voltage of a specimen can be measured based on an electrostatic capacitance between the two parts of the divided electrode plate. The electrode plate is used for applying a retarding voltage and arranged over a specimen.

That is, the present invention is to provide a scanning electron microscope including: an electron beam source; a stage for retaining thereon a specimen to which an electron beam from the electron beam source is irradiated; an objective lens for focusing the electron beam to the specimen retained on the stage; an electrode plate being arranged between the specimen and the objective lens, and having a passing aperture of the electron beam; and a retarding power supply used for decelerating the electron beam from the electron beam source until the electron beam comes to have a desired voltage by applying a voltage between the specimen and the electrode plate. The scanning electron microscope is characterized in that: the electrode plate is divided into at least two regions which are insulated from one another; an electrostatic capacitance between one of the regions which is electrically connected to the specimen, and the other region or an entirety of the other regions is measured; and an electrostatic voltage of the specimen is detected based on a measurement value thereof.

The scanning electron microscope of the present invention is characterized by further including: means for detecting a height of the specimen; and means for focusing an electron beam on the specimen by controlling, based on detected height information of the specimen, the retarding power supply and the objective lens.

The scanning electron microscope of the present invention is characterized in that the regions into which the electrode plate is divided are connected with one another through an insulating material.

As has been described hereinabove, according to the scanning electron microscope of the present invention, speedy focusing becomes possible because the scanning electron microscope is enabled to automatically measure an electrostatic voltage of a surface of a wafer inside a specimen chamber in an accurate, and easy speedy manner, the wafer assuming different electrostatic voltages inside and outside the specimen chamber.

DETAILED DESCRIPTION OF THE PREFERRED EMBODIMENT

Figure 1:
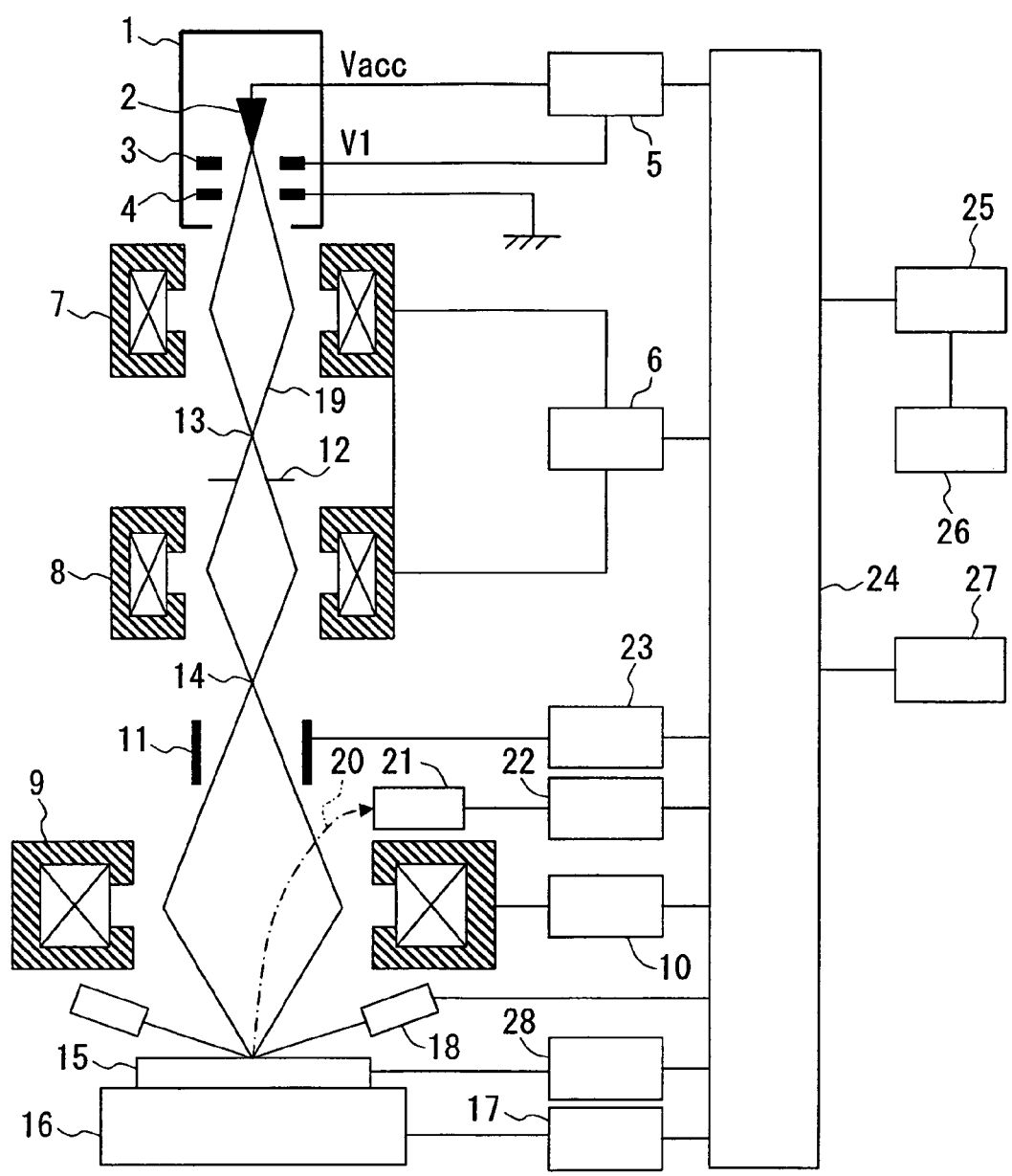
FIG. 1 is a view schematically showing an entire constitution of a scanning electron microscope of the present invention.

A best mode for carrying out the scanning electron microscope of the present invention will be described in detail hereinbelow with reference to the drawings. FIGS. 1 to 4 are views exemplifying an embodiment of the present invention. In these drawings, corresponding elements are indicated by parts to which corresponding reference numerals are given, and basic configuration and operations of elements corresponding to each other are assumed to be the same.

FIG. 1 is a view schematically showing an entire constitution of the scanning electron microscope of the present invention. In FIG. 1, the scanning electron microscope assumes a configuration for irradiating an electron beam to a specimen 15 placed on a specimen stage 16 from an electron gun 1 which includes an electron source 2, an extracting electrode 3 and an accelerating electrode 4. On an optical path of the electron beam, a first focusing lens 7 and a second focusing lens 8 which are driven by a focusing lens power supply 6, and an objective lens 9 which is driven by an objective lens controlling power supply 10, are arranged in order that the electron beam can be focused on the specimen 15 placed on the specimen stage 16. The specimen stage 16 is driven by a stage drive controlling device 17.

In this scanning electron microscope, an extracting voltage V1 is applied, by an electron gun power supply 5, between the electron source 2 and the extracting electrode 3, and an electron beam 19 is extracted from the electron source 2, by this voltage, toward onto the specimen stage 16. An accelerating voltage Vacc is applied, by the electron gun power supply 5, between the accelerating electrode 4, which has been maintained at a ground potential, and the electron source 2, and the electron beam 19 is accelerated by this accelerating voltage Vacc. The accelerated electron beam 19 is focused so that a first crossover 13 can be generated, by the first focusing lens 7, between the first focusing lens 7 and the second focusing lens 8. Additionally, an unnecessary region of the electron beam 19 is removed by a diaphragm plate 12 which is placed between the first crossover 13 and the second focusing lens 8. Furthermore, this electron beam 19 is focused so that a second crossover 14 can be generated, by the second focusing lens 8, between the second focusing lens 8 and the objective lens 9. Furthermore, this electron beam 19 is focused, by the objective lens 9, on the specimen 15 which is found on the specimen stage 16. Information on height positions of the specimen 15 which have been detected by a Z sensor 18 is fed back to the objective lens 9, whereby automatic focusing is performed.

An electron beam scanning deflector 11 is arranged between the second crossover 14 of the electron beam 19 and the objective lens 9. This electron beam scanning deflector 11 is used for deflecting the electron beam 19 so that the specimen 15 can be two-dimensionally scanned by the focused electron beam 19. A scanning signal of this electron beam scanning deflector 11 is controlled by a deflector controlling power supply 23 in accordance with an observation magnification. Additionally, to the specimen 15, a negative voltage is applied, as a retarding voltage which decelerates the primary electron beam 19, by a variable deceleration power supply 28. The retarding voltage is arbitrarily changed by adjusting the variable deceleration power supply 28.

When the specimen 15 is scanned with the focused electron beam 19 irradiated to the specimen 15, secondary electrons 20 are generated from the specimen 15. The generated secondary electrons 20 are detected by a detector 21, and are amplified by a signal amplifier 22. An amplified detected signal is inputted to a rendering unit 25 through a control calculation unit 24, then is converted into a visual signal in the rendering unit 25, and then is displayed, on a specimen image display unit 26, as an image of a surface shape of the specimen. Through an input unit 27, an operator can perform control over each of the above described units, and also can designate any measurement point, and provide an instruction for dimension measurement.

Figure 2:
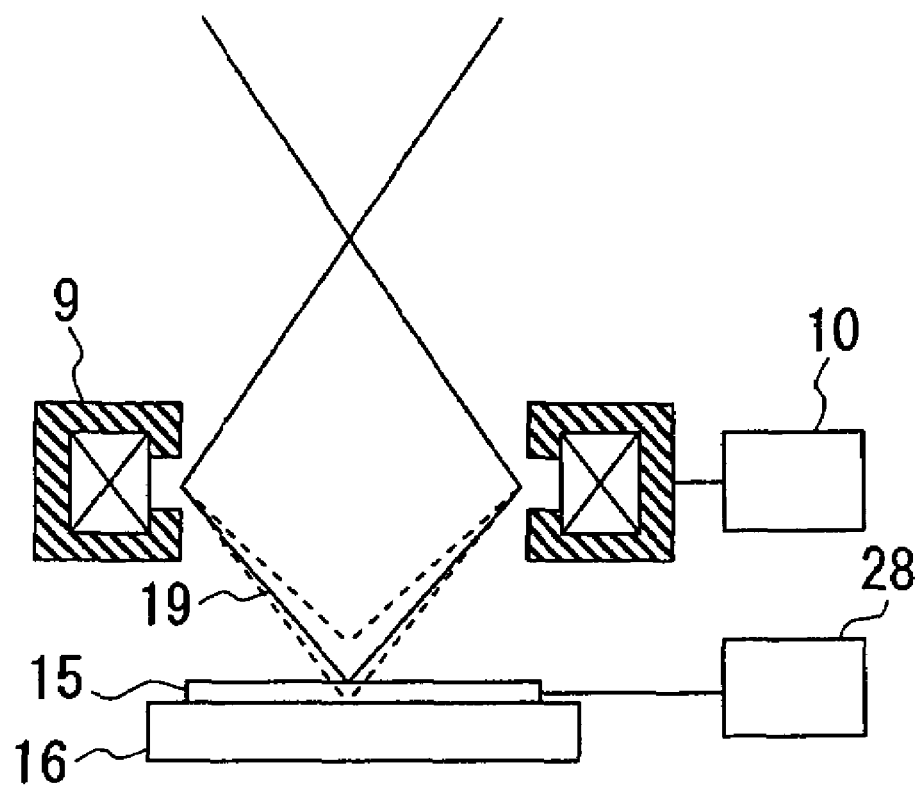
FIG. 2 is a view which explains focusing in the scanning electron microscope shown in FIG. 1.
Figure 3:
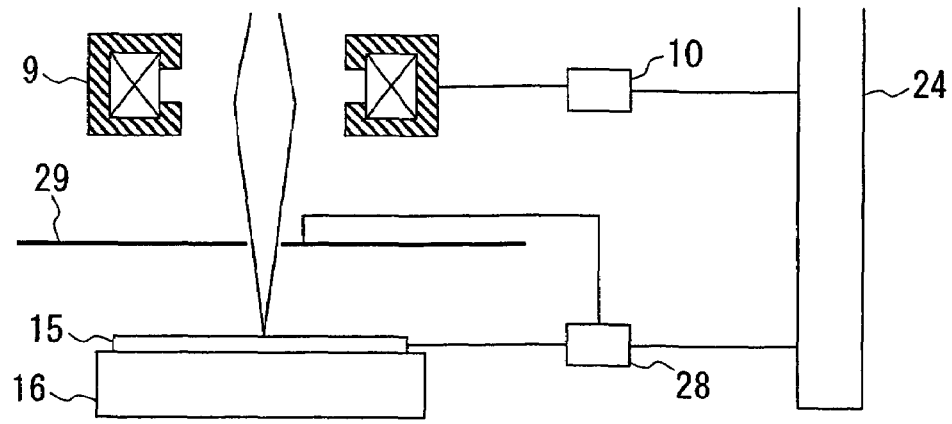
FIGS. 3A to 3C are enlarged views of areas surrounding the specimens in a conventional scanning electron microscope and in examples of the scanning electron microscope shown in FIG. 1
Figure 3:
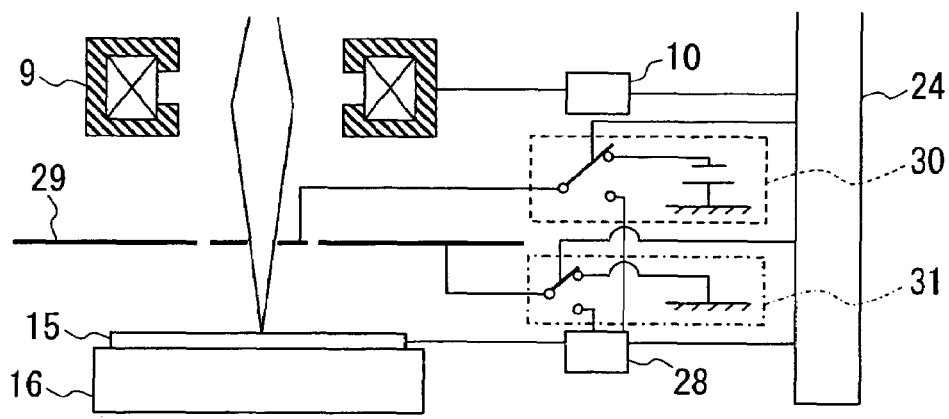
Figure 3:
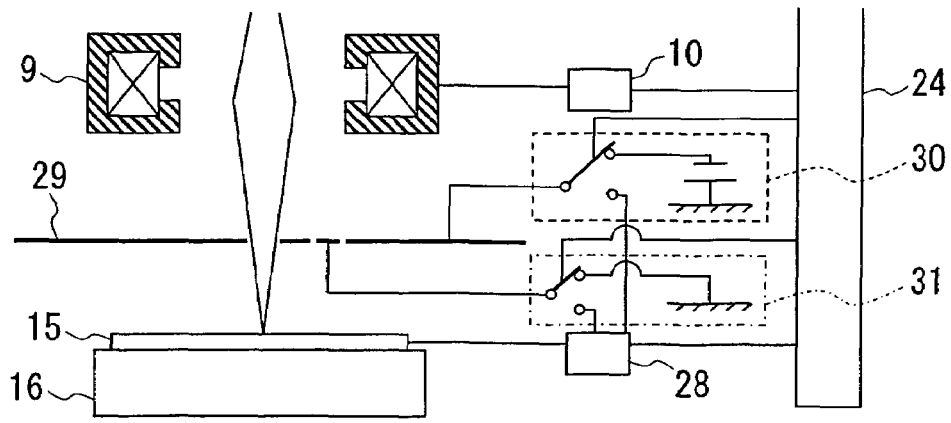
Figure 4:
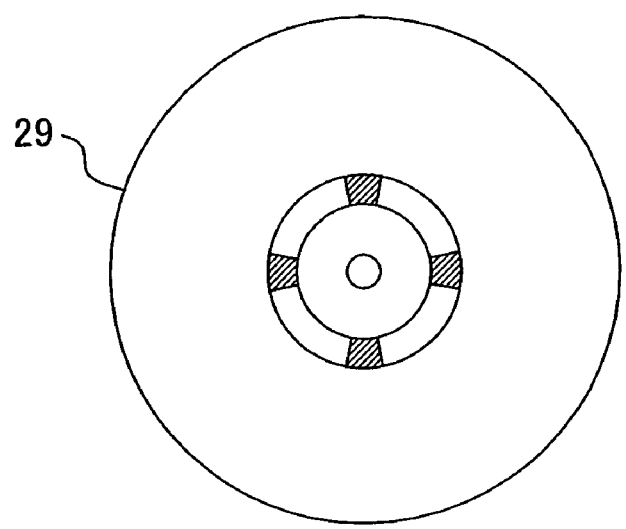
FIGS. 4A and 4B are plan views of electrode plates shown in FIGS. 3B and 3C.
Figure 4:
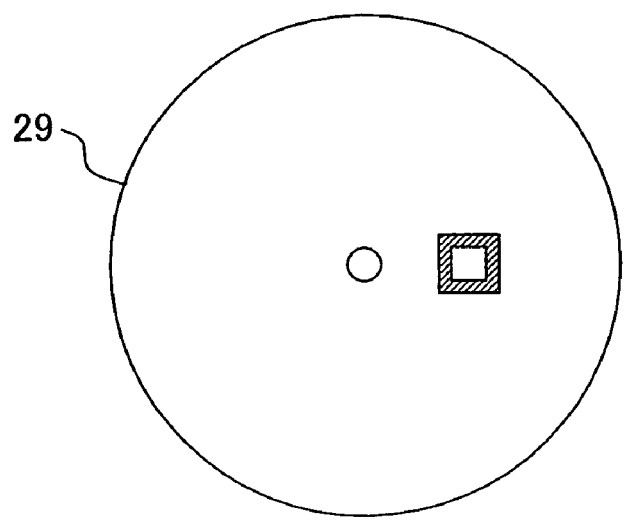

FIG. 2 is a view which explains focusing in the scanning electron microscope shown in FIG. 1. As has been described above, a condition of focusing on a wafer is determined by an accelerating voltage of the electron beam 19 irradiated to the wafer and a height of the wafer. When the specimen 15 is not electrically charged, the electron beam 19 is focused accurately on a surface of the specimen 15 in normal cases, as indicated by a solid line in FIG. 2. However, when the specimen 15 is electrically charged, a focused position changes from the focused position in normal cases as indicated by a broken line therein. If the focused position changes from on the specimen surface, the electron beam is brought out of focus, whereby detection of a measurement point ends in failure.

FIGS. 3A to 3C are enlarged views of areas surrounding the specimens 15 in a conventional scanning electron microscope and in examples of the scanning electron microscope shown in FIG. 1. In the conventional scanning electron microscope, an electrode plate 29 used for applying a retarding voltage is arranged above the specimen 15 as shown in FIG. 3A. In this configuration, voltages are controlled by the variable deceleration power supply 28 so that the electrode plate 29 and the specimen 15 can assume the same potential.

In contrast, as shown in each of FIGS. 3B and 3C, the scanning electron microscope of the present invention is characterized in that a part of the electrode plate 29 including an electron beam passing aperture, and the other part thereof are divided from each other, and those parts are connected to a switching circuit 30 and a switching circuit 31, respectively. Plan views of the electrode plates 29 shown in FIGS. 3B and 3C are shown in FIGS. 4A and 4B. In FIGS. 4A and 4B, the divided parts of the electrode 29 are assumed to be connected with each other through an insulating material. Or else, the divided parts of the electrode plate 29 may be isolated from each other and be separately retained.

In the scanning electron microscope of the present invention, by appropriately switching the switching circuit 30 and the switching circuit 31 connected respectively to the part of the electrode plate 29 including the electron beam passing aperture, and to the other part thereof as shown in FIGS. 3B and 3C, an electrostatic voltage of the specimen 15 can be measured based on an electrostatic capacitance between the two parts. By using a result of this measurement, focusing can be adjusted. On the other hand, when an image of the specimen 15 is obtained, it is only necessary to make the part of the electrode plate 29 including the electron beam passing aperture, and the other part thereof assume the same potential by connecting both of the switching circuit 30 and the switching circuit 31 to the variable deceleration power supply 28.

Accurate and speedy focusing on the specimen 15 can be performed by controlling each of the optical systems based on the thus accurately measured value of the electrostatic voltage of the specimen 15 inside the specimen chamber.

A specific example of a method of computing an electrostatic charge amount of the specimen 15 from the electrostatic capacitance between the divided parts of the electrode plate 29 is shown as follows:

Advance Preparation:

(1) Computing an electrostatic capacitance in a bare wafer by $$C = Q/V \qquad \text{equation 1}$$

(2) Computing a C-V line in the bare wafer

At the time of actual measurement:

(3) Measuring an electrostatic capacitance of the specimen by $$C' = Q'/V \qquad \text{equation 2}$$

(4) Computing C', from equations 1 and 2, by $$C' = C \times Q'/Q \qquad \text{equation 3}$$

(where C and Q are known from (1), and Q' is computed by $Q' = It$)

(5) Assuming a voltage variation with a change of C into C' to be a specimen electrostatic voltage, and calculating the voltage from the relational expression in (2).

In the above equations, Q denotes an electrical charge of the bare wafer; Q', an electrical charge of the specimen; C, an electrostatic capacitance of the bare wafer; C' an electrostatic capacitance of the specimen; V, a voltage; I, a current; and t, time.

Although the scanning electron microscope of the present invention has been described by showing the specific embodiment, the present invention is not limited to this. Those skilled in the art can add various alterations and improvements to configurations and functions according to the above embodiment without departing from spirits of the present invention.

What is claimed is:

1. Scanning electron microscope comprising:
an electron beam source;
a stage for retaining thereon a specimen to which an electron beam from the electron beam source is irradiated;
an objective lens for focusing the electron beam to the specimen retained on the stage;
an electrode plate being arranged between the specimen and the objective lens, and having a passing aperture of electron beam; and
a retarding power supply used for decelerating the electron beam from the electron beam source until the electron beam comes to have a desired voltage by applying a voltage between the specimen and the electrode plate,
wherein the electrode plate is divided into at least two regions which are insulated from one another,
an electrostatic capacitance between one of the regions which is electrically connected to the specimen, and the other region or an entirety of the other regions is measured,
and an electrostatic voltage of the specimen is detected based on a measurement value thereof.

2. The scanning electron microscope according to claim 1, further comprising:
means for detecting a height of the specimen; and
means for focusing an electron beam on the specimen by controlling the retarding power supply and the objective lens according to detected height information of the specimen.

3. The scanning electron microscope according to any one of claims 1 and 2, wherein the regions into which the electrode plate is divided are connected with one another through an insulating material.

* * * * *